United States Patent [19]

Zwaan et al.

[11] Patent Number: 5,062,145
[45] Date of Patent: Oct. 29, 1991

[54] IMPROVEMENTS IN OR RELATING TO HUMIDIFYING APPARATUS

[75] Inventors: Paul Zwaan; Ilija Orec; Charles G. Murray, all of Auckland, New Zealand

[73] Assignee: Fisher & Paykel Limited, Auckland, New Zealand

[21] Appl. No.: 412,819

[22] Filed: Sep. 27, 1989

[30] Foreign Application Priority Data

Sep. 29, 1988 [NZ] New Zealand ............ 226392
Oct. 31, 1988 [NZ] New Zealand ............ 226784

[51] Int. Cl.⁵ ............................................. F22B 1/28
[52] U.S. Cl. .................................... 392/396; 392/395
[58] Field of Search ............ 219/271, 272, 273, 274, 219/275, 276, 308, 374, 381, 382; 261/142, DIG. 65; 392/395, 396

[56] References Cited

U.S. PATENT DOCUMENTS

| 2,236,359 | 3/1941 | Armstrong | 219/273 |
| 3,616,796 | 11/1971 | Jackson | 128/212 |
| 3,871,373 | 3/1975 | Jackson . | |
| 4,101,294 | 7/1978 | Kimura | 48/77 |
| 4,532,088 | 7/1985 | Miller | 219/273 |
| 4,638,147 | 1/1987 | Dytch | 219/308 |
| 4,680,445 | 7/1987 | Ogawa | 219/308 |
| 4,753,758 | 6/1988 | Miller . | |
| 4,910,384 | 3/1990 | Silver | 219/271 |
| 4,913,140 | 4/1990 | Orec et al. . | |

FOREIGN PATENT DOCUMENTS 61-165534 7/1986 Japan .................... 219/272

Primary Examiner—Teresa J. Walberg
Attorney, Agent, or Firm—Trexler, Bushnell, Giangiorgi & Blackstone, Ltd.

[57] ABSTRACT

A humidifier of small gases passageway volume (of the order of 50 ml gases space) has a heater within a water containing envelope having a microporous wall common to the water space within the envelope and the gases space, the microporous wall being permeable to water vapour but not liquid water and the envelope being reinforced by a support which also directs the flow of gases over the surface of the envelope. The heater is wound as a flat spiral to avoid the effect of gases or water vapour bubbles on heater performance temperature.

40 Claims, 4 Drawing Sheets

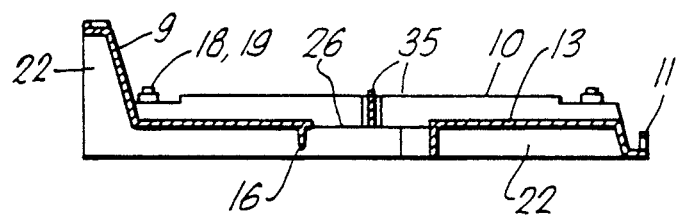
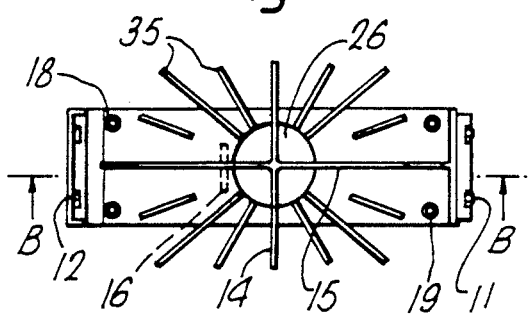
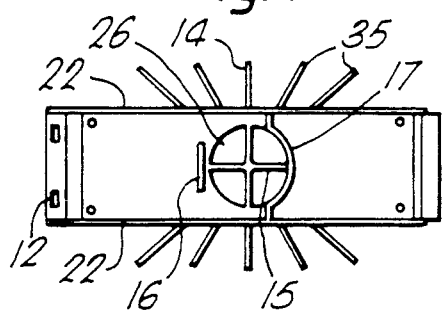
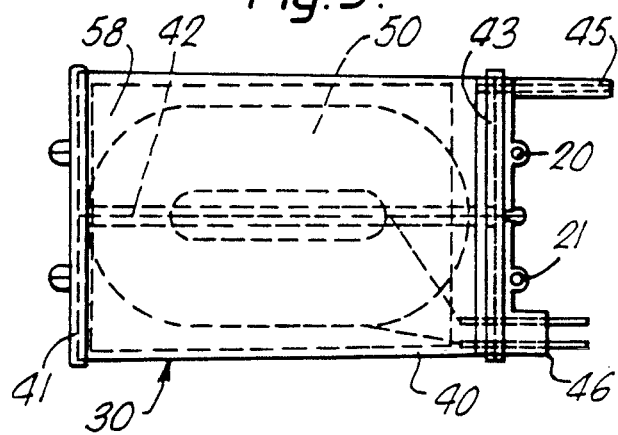
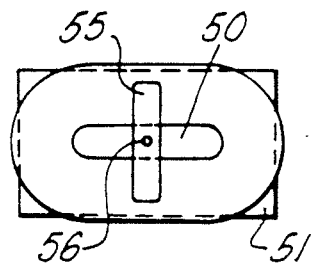

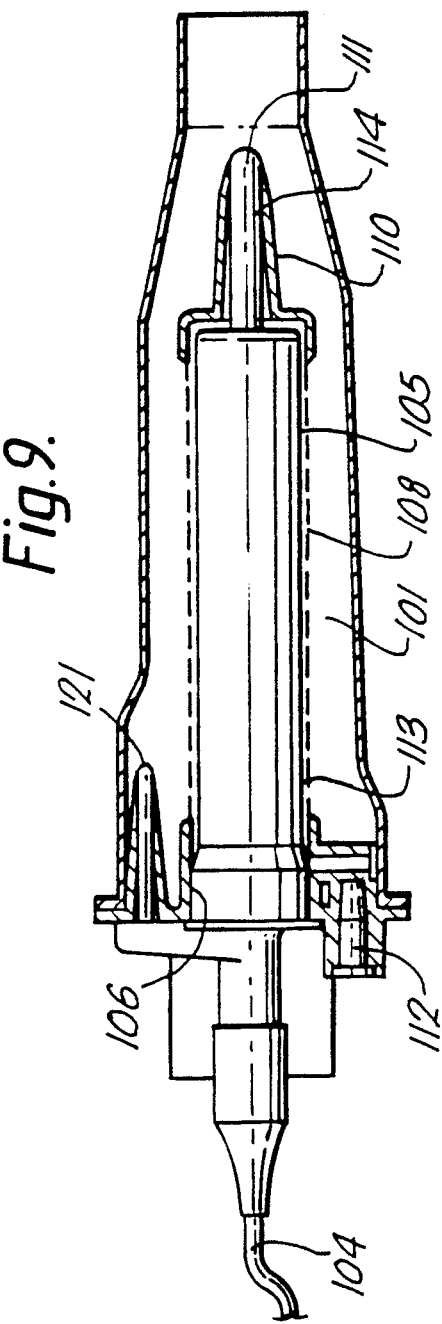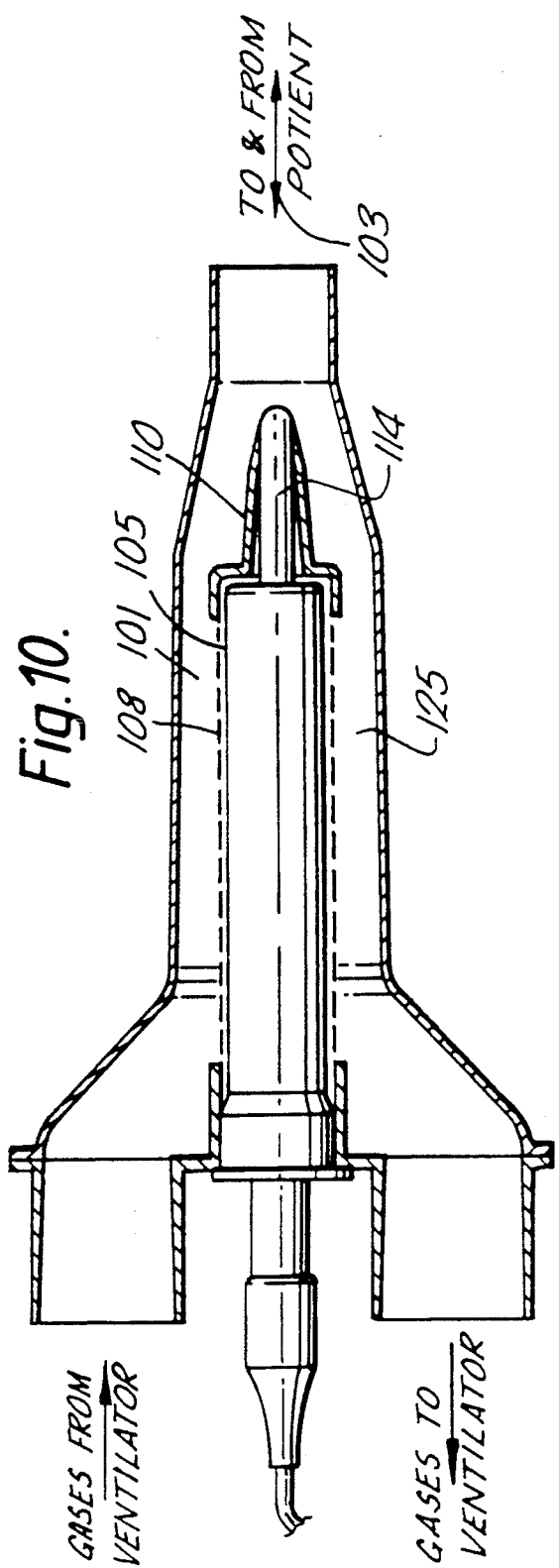

IMPROVEMENTS IN OR RELATING TO HUMIDIFYING APPARATUS

BACKGROUND OF THE INVENTION

This invention relates to humidifying apparatus and has been devised particularly though not solely for use in providing humidified gases to a patient in a hospital in need of such humidifying gases.

OBJECTS AND SUMMARY OF THE INVENTION

It is an object of the present invention to provide apparatus for humidifying gases which will at least provide the public with a useful choice.

Accordingly in one aspect the invention consists in apparatus for humidifying gases, said apparatus comprising a first passageway, a water supply inlet through which water is in use supplied to said first passageway, a second passageway through which gases are supplied to pass over a microporous wall common to both said first passageway and said second passageway at point of use, said microporous wall being permeable to water vapour but substantially impermeable to liquid water, heating means energisable to heat said water to generate vapour pressure within said first passageway sufficient to cause passage of water vapour but not liquid water through said microporous wall, the said microporous wall comprising sheet microporous material formed to a water compartment providing said first passageway and substantially contained by water compartment support means, said water compartment support means mechanically reinforcing said water compartment of microporous material to resist the pressures operating thereon.

In a further aspect the invention consists in the apparatus for humidifying gases, said apparatus comprising a first passageway, a water supply inlet through which water is supplied to said first passageway, a second passageway through which gases are supplied to pass over a microporous wall common to both said first passageway and said second passageway at point of use, said microporous wall being permeable to water vapour but substantially impermeable to liquid water, heating means energisable to supply heat to said water to generate vapour pressure within said first passageway sufficient to cause passage of water vapour but not liquid water through said microporous wall, a first heat sensing device being provided adjacent the one end of said first passageway and a second heat sensing device is provided adjacent the other end of said first passageway.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

A preferred form of the invention and modifications thereof will now be described with reference to the accompanying drawings in which;

FIG. 2 is a section elevation of part of a water compartment supporting means,

FIG. 3 is a plan view of one surface of the water compartment supporting means shown in FIG. 2, FIG. 4 is a plan view of the opposite surface of the water compartment supporting means shown in FIG. 3, FIG. 5 is a plan view of the water compartment, FIG. 6 is a plan view of heating apparatus, FIG. 9 and 10 are cross sections mutually at right angles of a modified form of the invention and FIG. 11 is a diagramatic sketch of a microporous wall used in the humidifier shown in FIG. 9 and 10.

DETAILED DESCRIPTION OF THE PREFERRED EMBODIMENT

Figure 1:
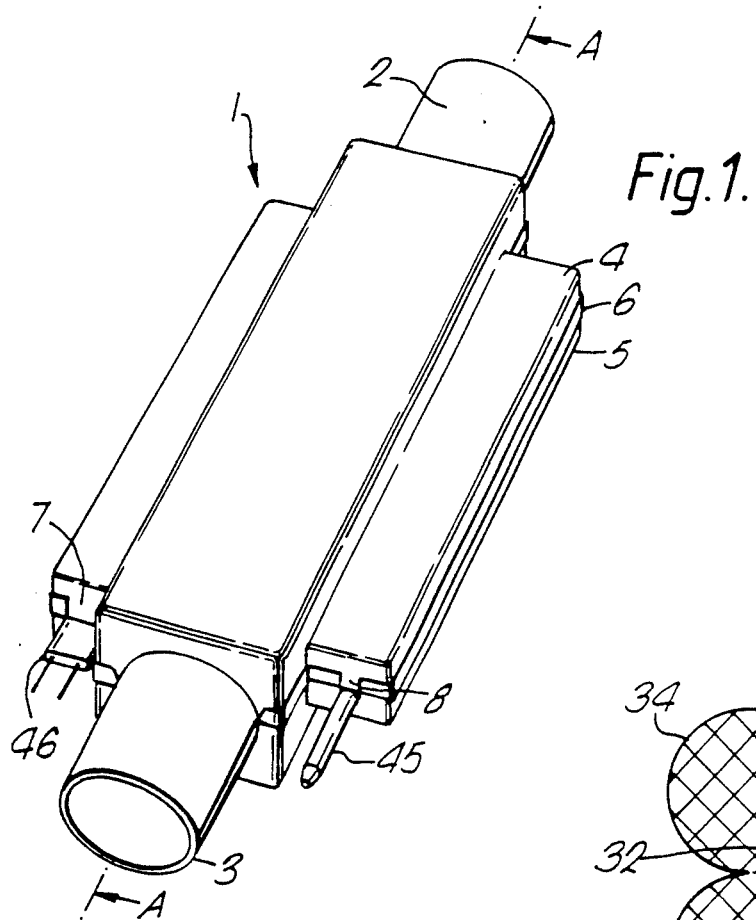
FIG. 1 is a diagrammatic isometric view of humidifying apparatus.

Referring to the drawings, apparatus for humidifying gases according to the present invention comprises a hollow body generally referenced 1, preferably made of a plastics material having a gases inlet 2 and a gases outlet 3, designed to be connected to tubular gas conduits between a supply of such gases and a patient.

The body 1 is assembled from a male hollow casing 4 and a female hollow casing 5, the female member 5 having an upwardly extending edge 6 (FIG.1)which surrounds an adjacent edge of the male member 4, enabling a gas tight seal to be made between the two members e.g. by use of an adhesive or a plastics solvent. The edge 6 of the female member 5 has a water entry tube receiving depression 8 and a electrical connection receiving depression 7 therein which in use provide access to apparatus contained within body 1 as described below. Alternatively, the male and female members may be joined perpendicular to the axis of the body rather than parallel to it.

Figure 7:
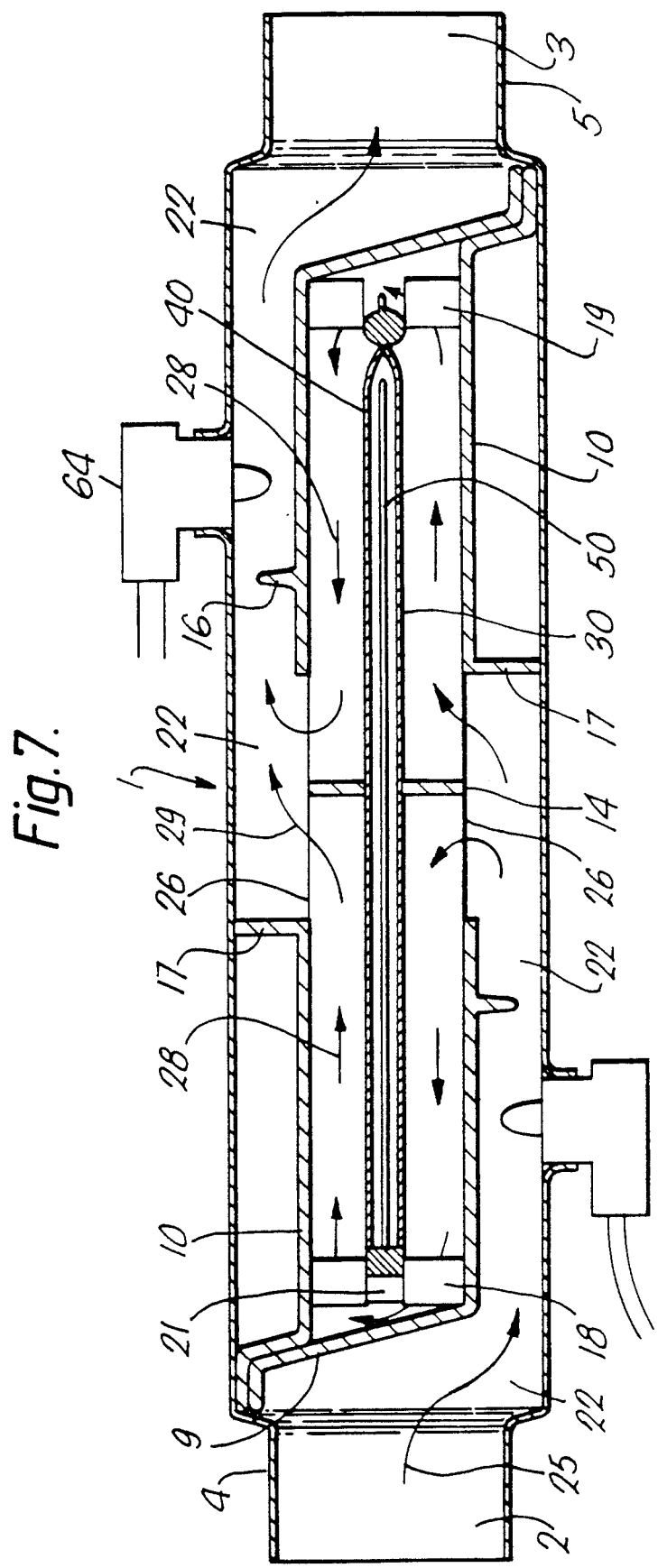
FIG. 7 is a sectional elevation of the humidifying apparatus, taken along line A—A of FIG. 1, some detail has been omitted for clarity.

The body 1 contains water compartment supporting means combined with gases flow directing means assembled from two water compartment supporting and flow distributing inner element members 10 (FIGS. 3 and 4). The members 10 are connected in such a way that the pins 11 of one member 10 are inserted into the locating slots 12 of a second member 10. One of the functions of the members 10 is to provide flow directing means to direct gases flow over the outer surface of the water compartment 30. Accordingly each member 10 has a transverse baffle member 9 seen in cross section in FIGS. 2 and 7, a series of radiating fins 35 on one face of a main surface 13, including a pair of intersecting fins 14 and 15 which pass over a gases flow aperture 26, and on the opposite side of main member 13 an aperture shielding baffle 17 which directs gases flow into or out of the gases flow aperture 26. Side members 22 also act in directing gases flow as will be explained further below. The resulting assembly having holes 26 coaxially aligned is shown in cross section within body 1 in FIG. 7. Referring to FIGS. 3 and 4 a baffle 16 is provided on member 10 for mixing the gases thoroughly prior to measuring their temperature with probe 64, the purpose of which is discussed later. Each member 10 also has mounting locators 18 and 19 (FIGS. 2, 3 & 7) which are designed to accommodate mounting tabs having apertures 20 and 21 on the water compartment 30 (FIG. 5).

The fins 35, 14 and 15 of member 10 provide structural support and rigidity to the assembled apparatus and in particular provide support for the water compartment 30 and also direct gases flow over the surfaces of the water compartment 30 as described below. Thus the free edges of the fins 35, 14 and 15 and of the side members 22 engage inner surfaces of the appropriate casing 4 or 5.

The water compartment 30 is constructed from microporous sheet material 40 having sealed edges 41, 42 and 43. The microporous material 40 is substantially permeable to water vapour but substantially impermeable to liquid water and is made from, for example, expanded PTFE (Polytetrafluoroethylene). Such sheet material is manufactured under the trade mark GOR-TEX and is available from W. L. Gore & Associates, Inc. Newark, Del.,U.S.A. in various thicknesses and dimensions.

To form the microporous walled water compartment 30 the sheet material 40 is cut into a rectangular shape, folded, and the edges fixed to each other for example by injecting a plastics material about the contacting edges to produce sealed edges 41, 42 and 43. The plastics material of sealed edges 41 and 43 provides mounting means comprising tabs 20 and 21. A water entry tube 45 and electrical contacts 46 are provided in the plastics material of sealed edge 43, which are connected to heating means comprising an electrical heating element 50, located within the water compartment 30.

In the preferred form of the invention the heating element 50 is provided as a flat spirally wound element in the form of an elongated disc wound preferably from enamelled copper wire preferably with turns epoxied or otherwise bonded to each other. The reason for providing the flat spiral arrangement is that in some circumstances air, gas or water vapour can be occluded within the water compartment 30 and if parts of a heating element are in an air bubble formed by that occluded air then the heating element would heat up perhaps damaging in that area. We have found that if a plurality of turns of wire are partially exposed to air then because of conductivity from the portions of turns in air to portions of turns in water, and to adjacent turns if epoxied together a lesser damaging effect is given compared with a whole turn of, for example ,a rod type heating element in which full turns are exposed to air and therefore run the risk of over heating.

Alternatively the heating element may comprise a printed circuit or etched-foil format on a rigid or preferably flexible substrate (e.g. Kanthal or Minco types); or alternatively a semiconducting material (as for example used in PTC heaters made by Hartford Eichenauer or TDK Corporation) or a composite of insulating and conductive materials such as carbon-filled plastics or carbon-filled synthetic rubbers (e.g. Premix Oy, or Jamak Inc respectively). These latter materials may be made into a suitable shape (e.g. a rectangle) with suitably connected metal electrodes (e.g. inserted or crimped down to opposite edges) to form a non-wound heater with suitable positive temperature coefficient of resistance to facilitate temperature measurement by resistance measurement and have some degree of temperature self-limiting due to resistance increase at elevated temperatures.

The heating element 50 may be encapsulated by or bonded to a heatsink 51 (FIG. 6), comprising a quantity of thermally conductive heatsink material, preferably metal (e.g. brass) positioned within the compartment 30. In the preferred form this is rectangular in shape with rounded edges/corners and is thermally bonded to the element with heat-bonding epoxy. The purpose of the heatsink 51 is to spread the heat evenly, further preventing hotspots.

The heatsink 51 may also provide a site for overheat sensing. In the preferred form of the invention heatsink 51 provides an electrical contact for an overheat protector (FIG. 6) FIG. 6 illustrates one embodiment of the heatsink and overheat protector where the heatsink 51 forms one contact, the other being formed by a sprung (preferably)brass member 55 attached thermally and electrically to the heatsink with a solder having a suitable preferably low melting point, referenced 56.

Overheat protection could be provided otherwise e.g. by having a low melting point soldered joint or a low melting point link in the wire of the heating coil.

In order to disperse water across the element/heatsink surface under all conditions a sheath or layer(s) of absorbent material 58 may be located adjacent the heatsink 51 or element 50 within the water compartment 30. The material 58 is preferably made of cotton-based paper having superior wicking properties.

In assembling the parts to make the humidifier, the water compartment is fixed to a member 10 by placing the apertures 20 and 21 over the mounting locators 18 and 19. The second member 10 is then positioned as shown in FIG. 9 with the free edges of fins 35, 13 and 14 in contact with the water compartment 30 thus providing support and resistance to bulging to the compartment 30. The pins 11 engage in the slots 12 at each end of the members 10. The water connection 45 is placed in depression 8 and the electrical connections 46 placed in depression 7. This assembly is then placed in the female casing 5 and the male casing is placed over the assembly of members 10 and compartment 30 and the edge 6 of the casing 5 fixed to the male casing e.g. by adhesive, the adhesive also joining the two halves of the gases inlet 2 and outlet 3. As stated the free edges of pins 35, 14 and 15 baffles 17 and 9 and side members 22 contact inner faces of the casings to direct gases flow. The total assembly is seen in cross section in FIG. 7.

In operation water is fed to the water compartment 30 through water entry tube 45 and electrical power is supplied to element 50 through electrical contacts 46. Gases from a source (not shown) enter the inlet 2, where transverse baffle 9 of member 10 diverts the gases downwardly, as shown by arrow 25 in FIG. 7. The gases are then diverted through air flow hole 26 by the aperture shielding baffle 17 after which the gases contact the lower outside surface of water compartment 30, being directed over the surface of the microporous material 40 by the flow directing means comprising the fins 35, 14 and 15 (FIGS. 3 and 4). Having passed over the lower outside surface of the water compartment 30, gases pass around the edges of the water compartment 30 so as to come into contact with the microporous material 40 of the upper outside surface of the water compartment 30. The fins 35, 14 and 15 of the upper member 10 also direct the gas flow back over the upper outside surface of the water compartment 30 as shown by the arrows 28 in FIG. 7, directing the gas flow through upper air flow hole 26 in the upper member 10. Aperture shielding baffle 17 of the upper member 10 diverts the gases toward the gases outlet 3, as shown by arrow 29 in FIG. 7, ensuring that the gases pass the temperature probe 64 behind baffle 16 of member 10. The location of the temperature probe 64 is arranged to optimise accuracy of average gas temperature measurement across the outlet part, over a wide range of airflows and passageway orientations. The temperature probe comprises for example a thermistor or other temperature measuring or indicating device.

This has the advantage that should there be overheating of the gases for any reason, the probe will transmit a suitable signal to control apparatus (not shown) which will cause appropriate operation of either the heating element or the flow of gases or otherwise to control the flow of gases water or heat so as to assist in ensuring the safe supply of humidified heated gases to a destination e.g. a hospitalised patient.

The control of heat and water supplied to the water compartment 30 is substantially in accordance with our New Zealand patent specification No. 212163 (U.S. Pat. No. 4,708, 831), the contents of which are incorporated herein by this reference. In addition, a second temperature probe at the gas inlet may be used to detect stationary or backwards flow of gases through the chamber by measuring the relative rise in temperature at this point and a corresponding drop in temperature at the outlet sensed by the first probe. This additional feature enables the heating and humidification of the gases to be synchronised with breathing of the patient, as well as terminating humidification when the gas flow is stopped or disconnected.

It will be seen that by the foregoing there is provided a construction in which the humidifying apparatus is kept to small dimensions. FIG. 1 shows somewhat to scale that the length of the apparatus is only a few times the diameter of the inlet 2 and exit 3, thus the device may only be about five to seven times such diameter and the width may only be of the order of two to three times the diameter of the inlet 2 and exit 3 and the thickness only slightly greater than such diameter. This corresponds to a volume of only 70 ml. The water compartment 30 and the members 10 have a volume of the order of 20 ml giving a gases space having a volume having a volume of the order of only 50 ml. Additionally because of the flat spirally wound heating element and heatsink the risk of overheating due to a single turn of such an element being exposed to an air bubble is minimised or at least reduced and an overheat sensor may be provided.

It will also be seen that because of the size and simplicity of the invention and the low cost plastics materials used, the constituent parts comprising the invention may be supplied as "throw away" items. This is a desirable feature with regard to patient hygiene in a hospital environment.

Figure 8:
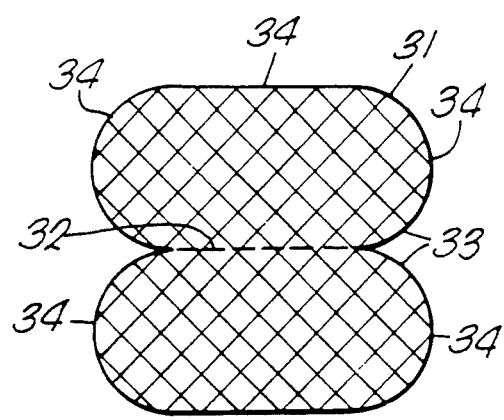
FIG. 8 is a plan view of an alterative form of microporous wall.

In a slightly modified form of the invention, to form the microporous walled water chamber 30 sheet material 31 is shaped for example as shown in FIG. 8 so as to be foldable along a line 32 and the two halves 33 are then fixed to each other for example by injecting a plastics material about the contacting folding edges 34.

Figure 11:
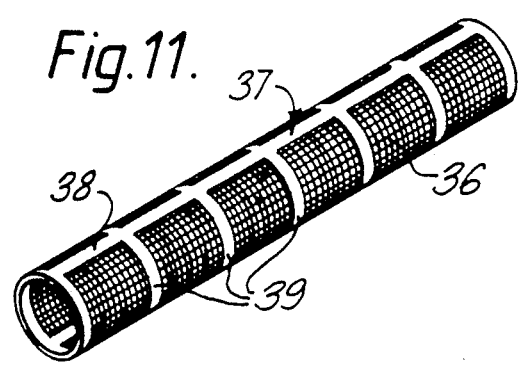

A further modified form of the invention which is shown in FIGS. 9 to 11 provides for heat and moisture exchanges between a patient and a gases supply.

Referring to FIGS. 9 and 10, a humidifying apparatus includes a second passageway 101, which is connected to a source of gases from a ventilator or similar device from which such gases are supplied to a patient, the supplied gases being indicated by the arrow. Mounted within the second passageway 101 is a first passageway 105, and that first passageway has a wall 108 common with the second passageway, such wall 108 comprising a microporous sheet material substantially permeable to water vapour but substantially impermeable to liquid water. The microporous membrane wall 108 is also made from for example expanded PTFE (polytetrafluoroethylene), which sheet material is also manufactured under the trade mark GOR-TEX and is available from W. L. Gore & Associates Inc. Newart Del. U.S.A. in various thickness and pore dimensions. To assist in resisting the operating pressure, the microporous wall 108 is covered or has incorporated therein a woven or unwoven reinforcing perhaps in the form of a lattice which might be referred to as a screen lattice (not shown). In addition the sheet material is formed into a tubular form and the tubular material 36 (FIG. 11) is insert moulded into a cage 37 having longitudinal 38 and circumferential bars 39 with the longitudinal joint between the longitudinal edges of the material incorporated in one of the longitudinal bars of the cage 37. In this way a tube is supplied which is reasonably reinforced to withstand the pressures operating yet which has areas through which the water vapour but not liquid water can pass. This is arranged by adjusting the relevant pore size, hydrophobicity and thickness of the microporuus material.

Arranged at the end of the tube 108 is a hollow extension 110. A connector 112 is provided through which water is supplied from a suitable supply such as a water supply bag feeding a drip chamber and contolled substantially in accordance with our aforesaid New Zealand patent application no. 212163 (U.S. Pat. No. 4,708,831). The heater 113 is sealed at 106 to the first passageway 105.

Within the first passageway 105 there is provided a means for heating water conveyed into the first passageway 105 through the connector 104. Such heater 113 may be a "throw-away" or preferably a reusable heater and preferably comprises a former which has wound on it many turns of a conductive material, preferably aluminum, or copper or alternatives discussed previously, to provided adequate surface area not materially less than the surface area of the microporous tube 108 through which vapour is passed. By applying a suitable low voltage, sufficient resistance can be incorporated in the wire to provide reasonable current carrying rating and a reasonable wattage rating for the heater 113. The heater 113 has an extension 114 which carries a primary temperature sensor such as a thermistor 111 at the distal end of the extension 114. The extension 114 fits in the follow extension 110. A secondary thermistor 121 is provided at the incoming gases end of the apparatus, and the two thermistors 111 and 121 provide information to control apparatus so as to control the temperature of the gases passing through the device.

The passageway 105 is preferably provided as a "throw away" apparatus and accordingly may be readily removed.

The above apparatus has the considerable advantage of providing a good surface area of microporous tube through which water vapour can pass but substantially no liquid water can pass and the whole apparatus is contained in a tube which can be kept close to the patient, thus avoiding difficulties with cooling of the gases after having been humidified and which ma cause condensation with consequent undesirable results. Positioning the humidifier in the 'deadspace' between the 'wye' and the patient can also reduce the amount of flow to be humidified, overcoming limitations placed on humidifier performance by high flows which in some modes of operation e.g in constant positive airway pressure(PAP) mode, can by pass the patient. In FIG. 9, gases flow into the second passageway 101 through inlet 112 and largely encompass the tube 108.

As may be seen from FIG. 9, the arrangement may be provided in the stem 125 of a Y function. The arrangment shown is provided in one leg of the Y function with suitable valving (not shown but usually provided by the breathing machine) so that when the patient breathes in, the gases pass over the humidifier above described and when the patient breathes out, the exhaled gases are diverted to another branch of the Y thus reducing rebreathing by the patient of already breathed gases and restricting flow over the humidifier to one direction only.

The construction has the advantage of being relatively simple yet providing the major advantage of the microporous wall arrangement.

From previous work which we have done in arriving at a satisfactory solution to the problem of successfully utilising the microporous wall arrangement we have found great difficulty in controlling the passage of liquid water through the microporous wall into the first passageway which of course can have deleterious results with and perhaps dangerous results for a patient. The above modified form of the present invention is directed to solving this problem in a simple yet effective manner.

What is claimed is:

1. Apparatus for humidifying gases, said apparatus comprising a first passageway, a water supply inlet through which water is in use supplied to said first passageway, a second passageway through which gases are supplied to pass over a microporous wall common to both said first passageway and said second passageway at point of use, said microporous wall being permeable to water vapour but substantially impermeable to liquid water, heating means energisable to heat said water to generate vapour pressure within said first passageway sufficient to cause passage of water vapour but not liquid water through said microporous wall, said microporous wall comprising sheet microporous material formed into a water compartment of microporous material providing said first passageway and substantially contained by water compartment support means, said water compartment support means mechanically reinforcing said water compartment of microporous material to resist the pressures operating thereon, said water compartment of microporous material formed to provide a flattened microporous tube with adjacent cut edges sealed or molded together, said heating means comprising a plurality of turns of an insulated electro conductive material arranged in a formation and positioned in said water compartment such that any air bubbles forming in water in said compartment encompass a plurality of turns with the likelihood of any single turn being encompassed by such air bubbles being obviated or minimised.

2. Apparatus as claimed in claim 1 wherein changes in resistance of said electro conductive material resulting from changes in temperature are used to provide signals indicative of the temperature of said heating means.

3. Apparatus as claimed in claim 1 wherein said turns of electro conductive material are bonded together.

4. Apparatus as claimed in claim 1 wherein said turns of electro conductive material are bonded to a heat sink.

5. Apparatus as claimed in claim 1 wherein said electro conductive material is copper.

6. Apparatus as claimed in claim 1 wherein said second passageway includes flow directing means arranged to provide a tortuous path for gases to enter said apparatus and pass in divided from over said microporous wall for delivery from said apparatus.

7. Apparatus as claimed in claim 6 wherein said second passageway is made as a two element plastics passageway, an inner element within which said water compartment is mounted and an outer element containing said inner element, said inner element having central air gases entry and exit.

8. Apparatus as claimed in claim 7 wherein said inner element comprising a pair of inner element members each having said water compartment support means and said flow directing means as parts thereof.

9. Apparatus as claimed in claim 8 wherein radiating members on said inner element members function both as parts of said water compartment support means and said flow directing means.

10. Apparatus as claimed in claim 7 wherein said outer element is provided as a male body element and a female body element fixed to each other on assembly.

11. Apparatus as claimed in claim 7 where said second passageway is provided with a heat sensing device arranged to indicate the temperature of gases leaving the passageway, said heat sensing device being positioned close to said exit from said inner element.

12. Apparatus as claimed in claim 11 wherein a further heat sensing device is provided adjacent the end of said second passageway where incoming gases pass over said microporous tube, for the purpose of detecting direction or magnitude of gas flow.

13. Apparatus for humidifying gases as claimed in claim 1 wherein said heating means comprises a form having wound thereon heating windings comprising a length of resistance material provided so that said wound resistance material has a surface area disposed in proximity to the surface area of said microporous wall.

14. Apparatus for humidifying gases as claimed in claim 13 wherein said heating winding is made of copper.

15. Apparatus as claimed in claim 13 wherein said form carries an extension extending beyond the confines of said microporous tube and a heat sensing device is mounted at a distal end of said extension.

16. Apparatus as claimed in claim 13 wherein said form is tubular.

17. Apparatus as claimed in claim 16 wherein said microporous tube and said cage and heater are removable for disposal.

18. Apparatus as claimed in claim 1 wherein said first and second passageways are provided in a mounting arranged close to a point of use in relation to a patient.

19. Apparatus as claimed in claim 1 wherein the microporous tube is disposed within a case formed by the water compartment support means.

20. Apparatus as claimed in claim 1 wherein said microporous tube is insert moulded into said water compartment support means with a joint along the length of said microporous material lying within a continuous longitudinal bar of said water compartment support means.

21. Apparatus for humidifying gases, said apparatus comprising a body defining outer walls of a first main passageway and a second main passageway, an inlet to said first main passageway and a gases outlet from said second main passageway, inner walls defining a gases distribution chamber between said first main passageway and said second main passageway with a gases inflow opening in said inner walls between said first main passageway and said gases distribution chamber and a gases outflow opening in said inner walls between said gases distribution chamber and said second main passageway, a water chamber within said gases distribution chamber said water chamber having a water inlet and a first side and an opposite side thereof, a microporous wall common to both said gases distribution chamber and said water chamber, said microporous wall being permeable to water vapor but substantially impermeable to liquid water, heating means within said water chamber energisable to heat said water to generate vapour pressure within said chamber sufficient to cause passage of water vapour but not liquid water through said microporous wall, there being gases distributing spaces between outer surfaces of said microporous wall and inner surfaces of said gases distribution chamber with water chamber support means in said gases distributing spaces, said water chamber support means mechanically reinforcing said water chamber and said microporous wall to resist pressures operating thereon and flow directing means in said gases distributing spaces to spread the flow of gases from said gases inlet through said first main passageway said gases inflow opening into said gases distribution chamber first over said first side of said water chamber and then over said gases opposite side of said water chamber and through a gases outflow aperture to said second main passageway for delivery therefrom to a patient said heating means comprising a plurality of turns of an insulated electroconductive material arranged in a formation such and positioned in said water chamber in a manner such that any air bubbles forming in water in said chamber encompass a plurality of turns with the likelihood of any single turn being encompassed by such air bubble being obviated or minimized.

22. Apparatus as claimed in claim 21 wherein said turns of electro conductive material are bonded together.

23. Apparatus as claimed in claim 21 wherein said turns of electro conductive material are bonded to a heat sink.

24. Apparatus as claimed in claim 21 wherein said electro conductive material is copper.

25. Apparatus as claimed in claim 21 wherein said second main passageway includes flow directing means arranged to provide a tortuous path for gases to enter said apparatus and pass in divided form over said microporous wall for delivery from said apparatus.

26. Apparatus as claimed in claim 25 wherein said body is made of two plastic elements, an inner element within which said water compartment is mounted and an outer element containing said inner element, said inner element having central air gases entry and exit.

27. Apparatus as claimed in claim 26 wherein said inner element comprises a pair of inner element members each having said water chamber support means and said flow directing means as parts thereof.

28. Apparatus as claimed in claim 27 wherein radiating members on said inner element members function both as parts of said water chamber support means and said flow directing means.

29. Apparatus as claimed in claim 26 wherein said outer element is provided as a male body element and a female body element fixed to each other on assembly.

30. Apparatus as claimed in claim 26 where said second main passageway is provided with a heat sensing device arranged to indicate the temperature of gases leaving the second main passageway, said heat sensing device being positioned close to said exit from said inner element.

31. Apparatus as claimed in claim 30 wherein a further heat sensing device is provided adjacent the end of said second main passageway where incoming gases pass over sad microporous wall, for the purpose of detecting direction or magnitude of gas flow.

32. Apparatus for humidifying gases as claimed in claim 21 wherein said heating means comprise a form having wound thereon heating windings comprising a length of resistance material provided so that said wound resistance material has a surface area approaching the surface area of said microporous wall.

33. Apparatus for humidifying gases as claimed in claim 32 wherein said heating winding is made of copper.

34. Apparatus as claimed in claim 32 wherein said form carries an extension extending beyond the confines of said microporous wall and a heat sensing device is mounted at a distal end of said extension.

35. Apparatus as claimed in claim 32 wherein said form is tubular.

36. Apparatus as claimed in claim 21 wherein said microporous wall is insert moulded into said water chamber support means with a joint along the length of said microporous material lying within a continuous longitudinal bar of said water chamber support means.

37. Apparatus as claimed in claim 21 wherein said microporous wall and said water chamber support means and heater are removable for disposal.

38. Apparatus as claimed in claim 37 wherein said heater is included in said water chamber support means as a "throw away" article.

39. Apparatus as claimed in claim 21 wherein said first and second main passageways are provided in a mounting arranged close to a point of use in relation to a patient.

40. Apparatus as claimed in claim 21 wherein changes in resistance of said electro conductive material resulting from changes in temperature are used to provide signals indicative of the temperature of the heating means.

* * * * *